US011660803B2

(12) United States Patent
Suppes et al.

(10) Patent No.: US 11,660,803 B2
(45) Date of Patent: May 30, 2023

(54) APPARATUS AND METHOD FOR STERILIZING PLASTIC PREFORMS

(71) Applicant: KRONES AG, Neutraubling (DE)

(72) Inventors: Waldemar Suppes, Nittendorf (DE); Florian Geltinger, Donaustauf (DE)

(73) Assignee: KRONES AG

( * ) Notice: Subject to any disclaimer, the term of this patent is extended or adjusted under 35 U.S.C. 154(b) by 0 days.

(21) Appl. No.: 17/543,354

(22) Filed: Dec. 6, 2021

(65) Prior Publication Data

US 2022/0176610 A1 Jun. 9, 2022

(30) Foreign Application Priority Data

Dec. 4, 2020 (DE) .................... 10 2020 132 324.7

(51) Int. Cl.
*B29C 49/46* (2006.01)
*B29C 49/36* (2006.01)
*B29C 49/42* (2006.01)

(52) U.S. Cl.
CPC ............. *B29C 49/46* (2013.01); *B29C 49/36* (2013.01); *B29C 49/4205* (2013.01); *B29C 2049/4635* (2013.01)

(58) Field of Classification Search
CPC ............ B29C 2049/4635; B29C 49/46; B29C 49/42065; B29C 49/4205
See application file for complete search history.

(56) References Cited

U.S. PATENT DOCUMENTS

| 2010/0229895 | A1 | 9/2010 | Iwashita et al. ............. 134/22.1 |
| 2011/0133370 | A1 | 6/2011 | Engelhard et al. ........... 264/535 |
| 2012/0100238 | A1 | 4/2012 | Humele et al. ................ 425/90 |
| 2014/0158500 | A1 | 6/2014 | Voth et al. .................... 198/617 |
| 2014/0178250 | A1 | 6/2014 | Loy ................................. 422/28 |
| 2014/0325941 | A1 | 11/2014 | Knott et al. .................... 53/426 |
| 2016/0193775 | A1* | 7/2016 | Lewin .................... B29C 49/46 264/454 |

(Continued)

FOREIGN PATENT DOCUMENTS

| DE | 10 2008 038 143 | 2/2010 | ............ B29C 49/42 |
| DE | 10 2010 049 385 | 4/2012 | ............ B29C 49/42 |

(Continued)

OTHER PUBLICATIONS

German Search Report issued in German Patent Appln. No. 10 2020 132 324.7, dated Aug. 16.2021, with machine English translation, 15 pages.

(Continued)

*Primary Examiner* — Robert B Davis
(74) *Attorney, Agent, or Firm* — Hayes Soloway P.C.

(57) ABSTRACT

Apparatus for treating plastic preforms, having a heating device for heating the plastic preforms, having forming devices for forming the plastic preforms into plastic containers, and having a sterilization device for sterilizing the plastic preforms, wherein the sterilization device has at least one first sterilization unit which has a rotatable transport carrier and a plurality of holding devices arranged on this transport carrier for holding the plastic preforms, as well as a plurality of first application devices for acting upon the plastic preforms, and the sterilization device has a second sterilization unit.

19 Claims, 3 Drawing Sheets

(56) References Cited

U.S. PATENT DOCUMENTS

2016/0229108 A1    8/2016  Aoki ....................... B29C 49/46

FOREIGN PATENT DOCUMENTS

| DE | 10 2011 107 772 | 1/2013 | ............ B65B 55/04 |
|----|-----------------|--------|-------------------------|
| DE | 10 2012 112 158 | 6/2014 | ............ B65G 47/86 |
| DE | 10 2012 112 803 | 6/2014 | ............ B29C 49/42 |
| DE | 10 2012 112 946 | 6/2014 | ............ B29C 49/42 |
| DE | 10 2018 124 287 | 4/2020 | ............ A61L 2/20  |
| EP |       2 623 293 | 8/2013 |                         |

OTHER PUBLICATIONS

Extended European Search Report issued in EP 21208344.8-1012, dated Jun. 9, 2022, with machine English translation, 11 pages.

\* cited by examiner

Fig. 5 of the plastic preforms. Such plastic preforms are used in the prior art to be heated and later formed into plastic containers, such as plastic bottles.

APPARATUS AND METHOD FOR STERILIZING PLASTIC PREFORMS

BACKGROUND OF THE INVENTION

The present invention relates to an apparatus and a method for sterilizing containers, in particular plastic containers and in particular plastic preforms. Such plastic preforms are used in the prior art to be heated and later formed into plastic containers, such as plastic bottles.

Various procedures for sterilizing these plastic preforms are known from the prior art. For example, it is known to sterilize the plastic preforms by means of radiation such as, for example, electron radiation or X-ray radiation or UV radiation. In another concept, the plastic preforms are treated with a sterilizing substance such as peracetic acid or hydrogen peroxide.

For this purpose, it is known in the prior art that the containers are placed on a transport starwheel and are acted upon with a sterilization medium at this transport starwheel during their transport. In the prior art, for example, several of these transport starwheels are used in succession. Usually, a first transport starwheel is provided on which the plastic preforms are treated, followed by a further transport starwheel which only transports the plastic preforms and, on this transport starwheel is followed by a transport starwheel on which both transport and application of the plastic preforms takes place. These procedures have proven themselves technically, but require a relatively large amount of space within a container treatment system.

The present invention is therefore based on the object of reducing the space and/or the installation space for such systems. It is also intended to provide a means of making such treatments more efficient.

SUMMARY OF THE INVENTION

An apparatus according to the invention for treating plastic preforms has a heating device for heating the plastic preforms, wherein the heating device having a transport device for transporting the plastic preforms, and at least one heating device for heating the plastic preforms. Furthermore, the apparatus comprises a forming device arranged downstream of the heating device in a transport direction of the plastic preforms for forming the plastic preforms into plastic containers, and a sterilization device for sterilizing the plastic preforms.

According to the invention, the sterilization device comprises at least a first sterilization unit comprising a rotatable transport carrier and a plurality of first holding devices arranged on said transport carrier for holding the plastic preforms, as well as a plurality of first application devices for acting upon the plastic preforms with a flowable medium.

Furthermore, the sterilization device has a second sterilization unit which adjoins the first sterilization unit in the transport direction of the plastic preforms and which has a rotatable transport carrier and a plurality of second holding devices arranged on this transport carrier for holding the plastic preforms. In addition, this second sterilization unit has a plurality of second application devices for acting upon the plastic preforms with a flowable medium, wherein the plastic preforms are transferred directly from the first sterilization unit to the second sterilization unit.

It is therefore proposed in the context of the invention that the sterilization device is constructed in such a way that the plastic preforms are transferred directly from the first sterilization unit to the second sterilization unit. In particular, this means that the plastic preforms are transferred, for example, from a holding device of the first sterilization unit directly to a holding device of the second sterilization unit, whereas in the state of the art the plastic preforms are first transferred from the first sterilization unit to a transport device and from the latter in turn to the second sterilization unit.

Preferably, the flowable medium with which the first application devices are acting upon the plastic preforms is a sterilization medium and/or a cleaning medium. In particular, the flowable medium is a liquid medium and in particular an air mixture with liquid $H_2O_2$ and/or $H_2O_2$ process gas. However, peracetic acid would also be usable.

Preferably, the flowable medium with which the second application devices act upon the plastic preforms is a sterilization medium and/or a cleaning medium. In particular, the flowable medium is a liquid medium and in particular hydrogen peroxide or peracetic acid.

In the context of the invention, reference is made to sterilization units. However, it is noted that in addition to or instead of sterilization units, it could also be cleaning units which apply a cleaning medium to the plastic preforms. Preferably, however, the units are sterilization units. The sterilization device in its entirety could also be a cleaning device, but preferably it is a sterilization device.

It is possible that the first and the second sterilization units act upon the containers with the same sterilization medium and/or cleaning medium. However, it would also be possible for the first and second sterilization units to apply the same sterilization medium and/or cleaning medium to the plastic preforms.

Advantageously, the heating device is an infrared heating device and in particular an infrared oven. Preferably, the heating elements or heating devices of this heating device are arranged stationary and the plastic preforms are transported past these heating devices. However, the heating device could also be a microwave oven which heats the plastic preforms by acting upon with microwave radiation.

Furthermore, the heating device comprises a rotating device for rotating the plastic preforms with respect to the longitudinal directions. In this way, a more uniform heating is achieved.

In a further advantageous embodiment, the forming device is a blow molding machine and in particular a stretch blow molding machine. Preferably, this forming device has a plurality of forming stations into which the plastic preforms are fed and are formed there into the containers by means of a pressurized medium, in particular with the aid of blown air but optionally also with a corresponding beverage.

In a further preferred embodiment, the forming device comprises a plurality of rod-like bodies (so-called stretching rods) which are insertable into the plastic preforms in order to expand them in their longitudinal direction. Preferably, the forming stations of the forming devices further comprise so-called blowing nozzles which are preferably applicable to the mouths of the plastic preforms in order to expand them in this way.

The above-mentioned holding devices for holding the plastic preforms are, in particular, gripping clamps which hold the plastic preforms in a predetermined area, for example below or above their so-called support ring.

In a preferred embodiment, the plastic preforms can be transferred directly from a holding device of the first sterilization unit to a holding device of the second sterilization unit.

In the context of the present application, the sterilization device is understood to be the entire device which serves to sterilize and/or clean the containers. The sterilisation units are the individual aggregates of this device, i.e. in particular transport starwheels with holding devices and application devices arranged thereon.

In a preferred embodiment, the sterilization units are designed as treatment starwheels, i.e. they preferably have rotatable carriers on which the holding devices and/or application devices are arranged. It is possible that these sterilization units are equipped with special nozzles which fill and/or charge the interior of the plastic preforms with a sterilizing agent and, in particular, with hydrogen peroxide.

In a further advantageous embodiment, the sterilization device is arranged in the transport direction of the plastic preforms between the heating device and the forming device. This means that the plastic preforms are first heated in an oven and then sterilized in this heated state and subsequently also formed, for example blown, into the plastic containers.

It would also be conceivable that the sterilization device is arranged before the heating device, i.e. the plastic preforms are first sterilized and then heated.

The present invention is further directed to a sterilization device for sterilizing plastic containers and in particular plastic preforms, wherein the sterilization device comprises at least a first sterilization unit, which comprises a rotatable transport carrier and a plurality of first holding devices arranged on this transport carrier for holding the plastic preforms as well as a plurality of first application devices for acting upon the plastic preforms with a flowable sterilization medium, and the sterilization device comprises a second sterilization unit which in a transport direction of the plastic preforms follows the first sterilization unit and which has a rotatable transport carrier and a plurality of second holding devices arranged on this transport carrier for holding the plastic preforms and a plurality of second application devices for acting upon the plastic preforms with a flowable sterilization medium.

According to the invention, the plastic preforms can be transferred directly from the first sterilization unit to the second sterilization unit.

Furthermore, it is possible that a first rotatable carrier is provided on which the holding devices are arranged, and a second rotatable carrier on which the application devices are provided. Preferably, these two rotatable carriers are rotatable about the same axis of rotation. Preferably, these two transport carriers are also parallel to each other.

In a further preferred embodiment, a supply line is associated with each application device, which supplies the sterilization medium to this application device. In a further advantageous embodiment, the apparatus has a distribution device which distributes a sterilization medium to the individual supply lines and/or the individual application devices.

In a further advantageous embodiment, the distribution device is designed as a rotary distributor which, starting from a reservoir, distributes the sterilization medium to the individual application devices.

In a preferred embodiment, each first holding device is assigned exactly one first application device and/or each second holding device is assigned exactly one second application device. Preferably, the holding devices are arranged below the application devices.

In a further preferred embodiment, the first application devices thus rotate about the same axis of rotation as the first holding devices. Preferably, the second application devices also rotate about the same axis of rotation as the second holding devices.

Preferably, the first and/or the second sterilization unit comprises at least 10, preferably at least 20 and preferably at least 30 application devices and/or holding devices. In a further preferred embodiment, the first and or the second sterilization unit comprises at most 100, preferably at most 90 and preferably at most 80 application devices and/or holding devices.

In a further preferred embodiment, the first application devices and/or the second application devices are arranged on a rotatable carrier. This may be the same rotatable carrier on which the holding devices are also arranged. Preferably, however, the application devices are arranged in a different rotatable carrier than the holding devices.

In a further preferred embodiment, the sterilization device comprises a third sterilization unit which comprises a rotatable transport carrier and a plurality of holding means arranged on said transport carrier for holding the plastic preforms and a plurality of application devices for acting upon the plastic preforms with a flowable sterilization medium.

Preferably, this third sterilization unit is followed by the second sterilization unit. Particularly preferably, the plastic preforms can be transferred directly from the second sterilization unit to the third sterilization unit and/or, strictly speaking, from a holding device of the second sterilization unit to a holding device of the third sterilization unit.

In a further preferred embodiment, the first application devices are arranged in a first position with respect to a longitudinal direction of the plastic preforms and the second application devices are arranged in a second position with respect to the longitudinal direction of the plastic preforms and preferably the first and second positions differ from each other or are different.

Preferably, therefore, the first and the second application devices and/or components of the first and second application devices are arranged at different heights and positions. In this way, the first and the second application devices cannot collide with each other (in particular in a transfer area in which the plastic preforms are transferred from the first sterilization unit to the second sterilization unit). Preferably, elements of the application devices are thus arranged at different heights.

In a further preferred embodiment, the application devices and/or the holding devices of the third sterilization unit are also arranged at a different height (in the longitudinal direction) of the plastic preforms than the application devices and/or holding devices of the second sterilization unit.

In a further preferred embodiment, the first application devices and/or the second application devices and/or the third application devices have distributing elements for distributing the sterilizing agent to mouth regions of the plastic preforms, wherein these distributing elements preferably having a larger cross section than the mouth cross sections of the containers or plastic preforms to be sterilized.

In this way, the plastic preforms can be sterilized both externally and internally, in particular in the region of their mouth. Particularly preferably, these distribution elements have circular cross-sections. In a further preferred embodiment, these distribution elements are bell-shaped (with the opening in the direction of the plastic preforms).

In a further preferred embodiment, the distribution elements comprise deflection elements for introducing a sterilizing agent into the interior of the plastic preforms.

In a further preferred embodiment, the first application devices and/or the second application devices are movable with respect to the containers to be sterilized in a longitudinal direction of the containers. In this way, it is possible for the application devices to be guided, for example, closer to the mouths of the plastic preforms in order to make the application with the sterilizing agent more efficient. This can be done by moving the application devices in the longitudinal direction of the plastic preforms or by moving the plastic preforms themselves. In addition, a combination of the two movements is also conceivable.

In a further preferred embodiment, the first holding means are arranged in a first position with respect to a longitudinal direction of the plastic preforms and the second holding means are arranged in a second position with respect to the longitudinal direction of the plastic preforms and the first and second positions are different. For example, it is possible that the plastic preforms are first gripped by the first holding means below their support ring and then gripped by the second holding means above the support ring.

This also prevents a collision of the holding devices (in the transfer area of the plastic preforms). Furthermore, the third holding devices (i.e. the holding devices of the third sterilization unit) are preferably also arranged at a different height position relative to the holding devices of the second sterilization unit. In this way, a collision between the second holding devices and the third holding devices cannot occur.

Furthermore, the sterilization unit preferably comprises at least one valve device and preferably a plurality of valve devices. Preferably, at least one valve device is associated with each application device, so that the supply of the flowable medium to each individual plastic preform can be controlled separately. These valve devices can be arranged in a region of the application devices or also in other regions, such as in the vicinity of the rotary distributor.

In a further preferred embodiment, the sterilization device has a clean room within which the plastic preforms are transported. This clean room separates the transport path of the plastic preforms from a (non-sterile) environment during their sterilization. It is possible that all sterilization units are arranged within this clean room. Preferably, however, the heating device for heating the plastic preforms is arranged outside the clean room.

This clean room can have two walls which are movable in relation to each other and which delimit the clean room.

In a further preferred embodiment, the sterilization device comprises at least one pitch distribution device, such as in particular a pitch distribution starwheel, which is suitable and intended for changing and in particular increasing a pitch between transported plastic preforms. Preferably, this first pitch distribution device is arranged upstream of the first sterilization unit in the transport direction of the plastic preforms.

In a further preferred embodiment, the apparatus comprises a second pitch distribution device and preferably a second pitch distribution starwheel, which is also suitable and intended for changing and in particular increasing a pitch of the plastic preforms. Preferably, this second pitch distribution starwheel is arranged in the transport direction of the plastic preforms after the last, for example after the third sterilization unit.

The present invention is further directed to a method for sterilizing plastic containers and, in particular, plastic preforms, wherein the plastic preforms are sterilized by means of a first sterilization device comprising at least a first sterilization unit comprising a rotatable transport carrier and a plurality of first holding devices arranged on said transport carrier which hold the plastic preforms, and a plurality of first application devices which act upon the plastic preforms with a flowable medium.

Furthermore, the sterilization device comprises a second sterilization unit which sterilizes the plastic preforms after their sterilization with the first sterilization unit and which comprises a (second) rotatable transport carrier and a plurality of second holding devices arranged on this transport carrier which hold the plastic preforms as well as a plurality of second application devices which act upon the plastic preforms with a flowable medium.

According to the invention, the plastic preforms are transferred directly from the first sterilization unit to the second sterilization unit.

It is therefore also proposed on the method side that the plastic preforms are transferred directly from the first sterilization unit or from a holding device of the first sterilization unit to a holding device of the second sterilization unit.

In a preferred method, the plastic preforms are first heated in a heating device. Then, preferably, a pitch of the plastic preforms is changed and in particular increased.

Subsequently, the plastic preforms are sterilized by means of the first sterilization unit and in particular treated or acted upon with H2O2 process gas. In this process, the plastic preforms can be gripped, for example, below their support ring. In a further step, the plastic preforms are treated by means of the second sterilization unit, which is preferably also performed with H2O2 process gas. Preferably, the plastic preforms are gripped above their support ring.

Then, preferably, the plastic preforms are treated with the third sterilization unit, wherein here also preferably the treatment is carried out with H2O2 process gas. Preferably, the plastic preforms are again gripped below their support ring.

Subsequently, a pitch of the plastic preforms is optionally again further modified and in particular further increased by means of a second pitch distribution device, in particular in order to transfer the plastic preforms to a forming device such as in particular a stretch blow molding machine in a further step.

BRIEF DESCRIPTION OF THE DRAWINGS

Further advantages and embodiments will be apparent from the accompanying drawings.

In the drawings.

DETAILED DESCRIPTION OF THE INVENTION

Figure 1:
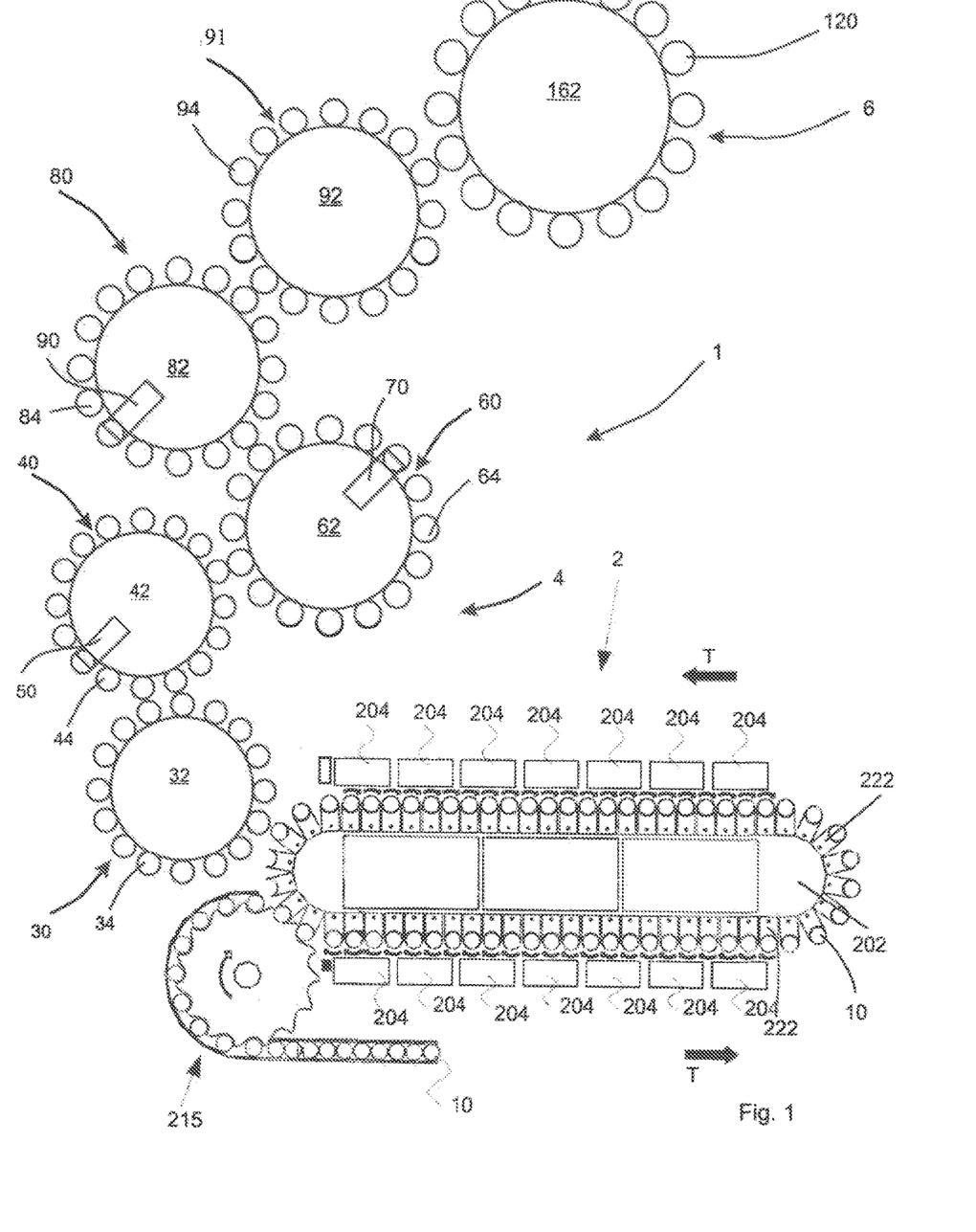
FIG. 1 shows a schematic representation of an apparatus for handling containers.

FIG. 1 shows a representation of an apparatus 1 for manufacturing containers. In this case, plastic preforms 10 are first supplied by means of a supply device 215 such as a clock-in starwheel to an oven designated in its entirety as 2. This oven 2 has a plurality of heating devices 204, which are arranged stationary along the transport path of the plastic preforms. The plastic preforms 10 are guided past these heating devices 204 by means of a transport device 202 and holding elements 222, and are heated thereby.

This heating device 2 is followed by a first transport device in the form of a pitch distribution starwheel 30. This increases the pitch between the individual plastic preforms, i.e. their distance from one another. This pitch distribution starwheel has a rotatable carrier on which a plurality of holding devices 34 for holding the plastic preforms are arranged. These are thereby preferably movable in such a way that the pitch between the plastic preforms 10 is changed and in particular increased or enlarged. This pitch distribution starwheel is thereby preferably already arranged within a clean room which is not shown, and is preferably also a component of the sterilization module. Preferably, the plastic preforms are transported clockwise by the pitch distribution starwheel.

This first transport device is followed by a sterilization device designated in its entirety as 4. This sterilization device comprises a first sterilization unit 40. This first sterilization unit 40 has a rotatable carrier 42, on which a plurality of holding devices 44 for holding the plastic preforms are arranged. In addition, a plurality of application devices (denoted in their entirety by 50) is provided for acting upon the plastic preforms with a sterilization medium such as hydrogen peroxide. Preferably, the plastic preforms are transported counterclockwise by the first sterilization unit 40.

The first sterilization unit 40 is followed by a second sterilization unit 60. This second sterilization unit 60 also has a rotatable transport carrier 62, as well as a plurality of holding devices 64 which also serve to hold the plastic preforms. In addition, this second sterilization unit 60 comprises a plurality of application devices 70 (only one shown) which also pressurize the plastic preforms with a (in particular flowable) sterilization medium. Preferably, the plastic preforms are transported clockwise by the second sterilization unit 60.

The second sterilization unit 60 is followed by a third sterilization unit 80. This also has a transport carrier 82, as well as a plurality of holding devices 84 which are arranged on this transport carrier 82. In addition, a plurality of application devices 90 (only one shown) is again provided here, which also acting upon the plastic preforms with a sterilization medium. Preferably, the plastic preforms are transported counterclockwise with the third sterilization unit 80.

Preferably, the third sterilization unit 80 is adjoined by a further transport device in the form of a second pitch distribution starwheel 91. This second pitch distribution starwheel also has a rotatable carrier 92, on which a plurality of holding devices 94 are arranged for holding the plastic preforms. This second pitch distribution starwheel also increases the pitch between the plastic preforms. In this regard, the second pitch distribution starwheel 91 may also still be part of the sterilization device 4 and may also still be arranged in the clean room (not shown). Preferably, the plastic preforms are transported clockwise by the second pitch distribution starwheel 91.

A forming device 6, such as in particular a stretch blow-molding machine, follows the sterilization device 4. This also has a transport carrier 162, as well as a plurality of forming stations 120, each of which forms the plastic preforms—in this case by applying compressed air—into the plastic containers.

Figure 2:
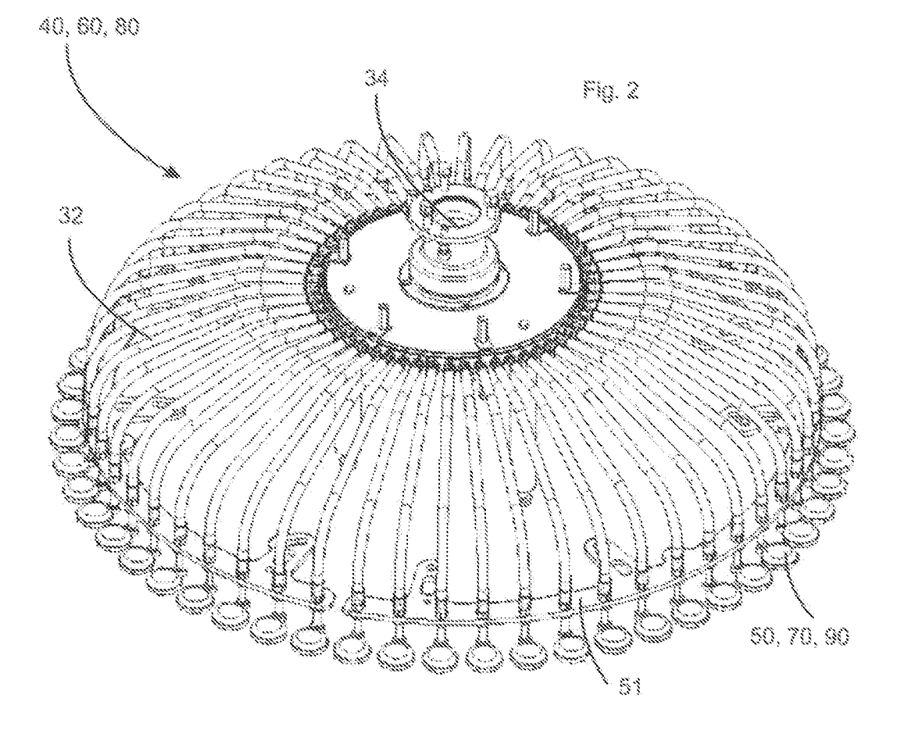
FIG. 2 shows a schematic representation of a sterilization unit.

FIG. 2 shows an illustration of a sterilization unit 40, 60, 80. These sterilization units can be of substantially the same design. The sterilization unit 40, 60, 80 has a plurality of application devices 50, 70, 90. The sterilizing agent is supplied to each of these via supply lines 32. The reference sign 34 indicates a distribution device, such as a rotary distributor, which distributes the sterilization medium to the individual application devices 50, 70, 90.

The reference sign 51 indicates a transport starwheel, which is only partially shown, on which the individual application devices are attached. It is possible that this transport starwheel is in turn fixed in the carrier 42, 62, 82 shown in FIG. 1, but it would also be possible that a further separate carrier, in particular a disc-shaped carrier, is provided, which is not shown in FIG. 2.

Figure 3:
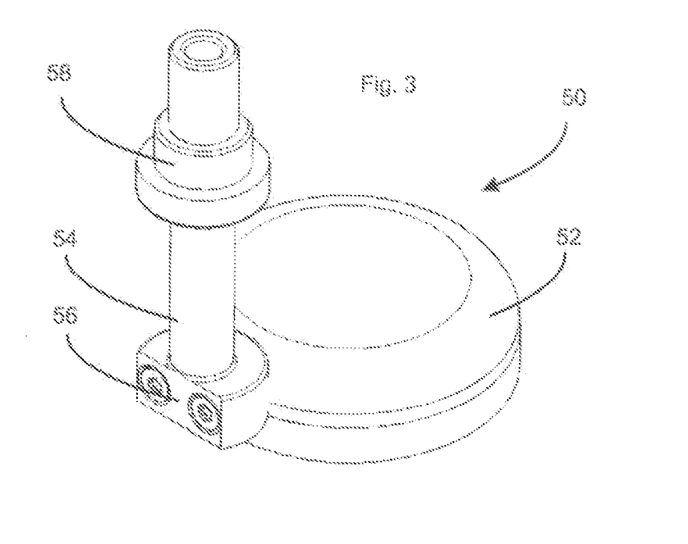
FIG. 3 shows an illustration of an application device.

FIG. 3 shows a sterilization unit 50, which has a supply line 54, which is arranged on a connection 58 and which supplies the sterilization medium via a deflection 56 to a distribution device 52. This distribution device guides the sterilization medium to the mouth area of the plastic preforms.

Figure 4:
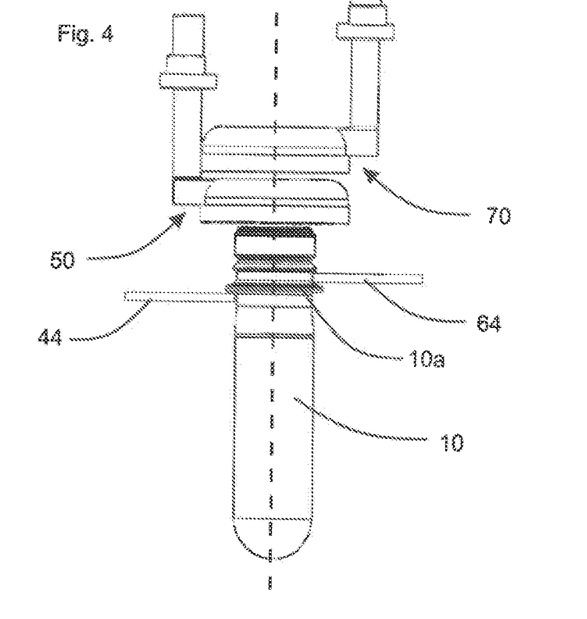
FIG. 4 shows a sectional view of two application devices in a transfer area.

FIG. 4 shows an illustration of a plastic preform 10 being guided in a transfer area in which it is transferred from a sterilization unit, for example the first sterilization unit 40, to another sterilization unit. Here, the reference sign L refers to the longitudinal direction of the plastic preform. It can be seen that, in this longitudinal direction L, the two application devices 50 and 70 are arranged one above the other in an offset manner so that they cannot collide with each other. Also, the holding devices 44 and 64 associated with the two sterilization units are arranged at different heights (offset) so that they can grip the plastic preform 10 below its support ring 10a on the one hand and above its support ring on the other hand. In this way, there can also be no collusion of the holding devices.

In addition, it is possible that in operation the application devices 50 or 70 are displaceable in the longitudinal direction L, but in particular in an area outside the shown transfer area. It should be taken into account that only one of the two application devices and only one of the two holding devices is provided outside the transfer area. For the purpose of bringing the application device towards the plastic preform, for example, the plastic preform 10 can be raised or, conversely, the application device 50 or 70 can be lowered.

Figure 5:
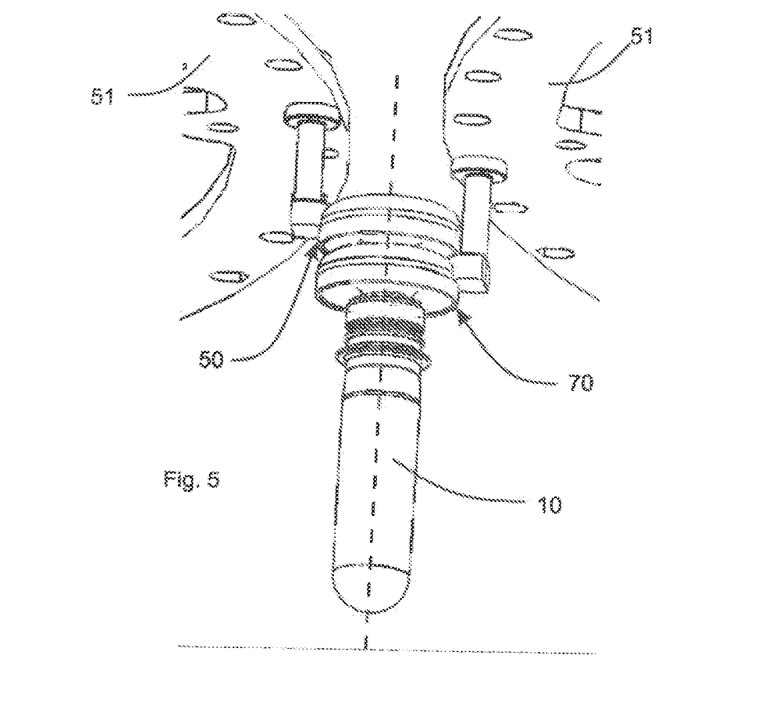
FIG. 5 shows a further illustration of the transfer of a plastic preform from one sterilization unit to another sterilization unit.

FIG. 5 shows a further illustration of the transfer of a plastic preform from a sterilization unit to a further sterilization unit. Here again the two carriers 51 are shown on which the respective application devices 50, 70 are arranged. It can be seen that there is no collision between the application devices in this transfer area.

The applicant reserves the right to claim all features disclosed in the application documents as essential to the invention, provided that they are individually or in combination new compared to the prior art. It is further pointed out that the individual figures also describe features which may be advantageous in themselves. The skilled person immediately recognizes that a particular feature described in a figure can be advantageous even without adopting further features from that figure. Furthermore, the skilled person recognizes that advantages can also result from a combination of several features shown in individual figures or in different figures.

The invention claimed is:

1. An apparatus for treating plastic preforms with a heating device for heating the plastic preforms, wherein the heating device has a transport device for transporting the plastic preforms and at least one heating device for heating the plastic preforms, having a forming device, arranged downstream of the heating device in a transport direction of the plastic preforms, for forming the plastic preforms into plastic containers, and having a sterilization device for sterilizing the plastic preforms, wherein the sterilization device has at least one first sterilization unit which has a rotatable transport carrier and a plurality of holding devices arranged on the transport carrier and configured for holding the plastic preforms, and a plurality of first application devices configured for acting upon the plastic preforms with a flowable medium, and the sterilization device has a second sterilization unit which follows the first sterilization device in the transport direction of the plastic preforms and which has a rotatable transport carrier and a plurality of second holding devices arranged on this transport carrier configured for holding the plastic preforms, and a plurality of second application devices configured for acting upon the plastic preforms with a flowable medium, wherein the plastic preforms are transferred directly from the first sterilization unit to the second sterilization unit, wherein the first application devices or components of the first application devices are arranged in a first position with respect to a longitudinal direction of the plastic preforms and the second application devices or components of the second application devices are arranged in a second position with respect to the longitudinal direction of the plastic preforms and the first and second positions are different.

2. The apparatus according to claim 1,
wherein
the plastic preforms are transferred directly from a holding device of the first sterilization unit to a holding device of the second sterilization unit.

3. The apparatus according to claim 1,
wherein
the sterilization device is arranged in the transport direction of the plastic preforms between the heating device and the forming device.

4. A sterilization device for sterilizing plastic preforms, wherein the sterilization device has at least one first sterilization unit which has a rotatable transport carrier and a plurality of first holding devices, arranged on the transport carrier and configured for holding the plastic preforms, and a plurality of first application devices configured for acting upon the plastic preforms with a flowable sterilization medium, and the sterilization device has a second sterilization unit which follows the first sterilization unit in the transport direction of the plastic preforms and which has a rotatable transport carrier and a plurality of second holding devices, arranged on this transport carrier and configured for holding the plastic preforms, and a plurality of second application devices configured for acting upon the plastic preforms with a flowable sterilization medium, wherein the plastic preforms can be transferred directly from the first sterilization unit to the second sterilization unit, wherein the first application devices or components of the first application devices are arranged in a first position with respect to a longitudinal direction of the plastic preforms and the second application devices or components of the second application devices are arranged in a second position with respect to the longitudinal direction of the plastic preforms and the first and second positions are different.

5. The sterilization device according to claim 4,
wherein
precisely one first application device is assigned to each first holding device and/or precisely one second application device is assigned to each second holding device.

6. The sterilization device according to claim 4,
wherein
the first application devices and/or the second application devices are arranged on a rotatable carrier.

7. The sterilization device according to claim 4,
wherein
the sterilization device comprises a third sterilization unit, which comprises a rotatable transport carrier and a plurality of holding devices arranged on this transport carrier for holding the plastic preforms, as well as a plurality of application devices for acting upon the plastic preforms with a flowable sterilization medium.

8. The sterilization device according to claim 4,
wherein
the first application devices and/or the second application devices have distributing elements configured for distributing a sterilizing agent to mouth regions of the containers, wherein the distributing elements having a larger cross section than the mouth cross sections of the containers to be sterilized.

9. The sterilization device according to claim 4,
wherein
the first application devices and/or the second application devices are movable with respect to the containers to be sterilized in a longitudinal direction of the containers.

10. The sterilization device according to claim 4,
wherein
the first holding devices are arranged in a first position with respect to a longitudinal direction of the plastic preforms and the second holding devices are arranged in a second position with respect to the longitudinal direction of the plastic preforms, and the first and second positions are different.

11. A method for sterilizing plastic preforms, wherein the plastic containers are sterilized by a first sterilization device which comprises at least a first sterilization unit which has a rotatable transport carrier and a plurality of first holding devices arranged on said transport carrier which hold the plastic preforms, and a plurality of first application devices which act upon the plastic preforms with a flowable medium, and the sterilization device has a second sterilization unit which sterilizes the plastic preforms after they have been sterilized by the first sterilization unit and which has a rotatable transport carrier and a plurality of second holding devices which are arranged on this transport carrier and hold the plastic preforms, and a plurality of second application devices which act upon the plastic preforms with a flowable medium, wherein the plastic preforms are transferred directly from the first sterilization unit to the second sterilization unit, wherein the first application devices or components of the first application devices are arranged in a first position with respect to a longitudinal direction of the plastic preforms and the second application devices or components of the second application devices are arranged in a second position with respect to the longitudinal direction of the plastic preforms and the first and second positions are different.

12. The apparatus according to claim 2,
wherein
the sterilization device is arranged in the transport direction of the plastic preforms between the heating device and the forming device.

13. The sterilization device according to claim 5,
wherein
the first application devices and/or the second application devices are arranged on a rotatable carrier.

14. The sterilization device according to claim 5,
wherein
the sterilization device comprises a third sterilization unit, which comprises a rotatable transport carrier and a plurality of holding devices arranged on this transport carrier for holding the plastic preforms, as well as a plurality of application devices for acting upon the plastic preforms with a flowable sterilization medium.

15. The sterilization device according to claim 5,
wherein
the first application devices or components of the first application devices are arranged in a first position with respect to a longitudinal direction of the plastic preforms and the second application devices, or components of the second application devices are arranged in a second position with respect to the longitudinal direction of the plastic preforms and the first and second positions are different.

16. The sterilization device according to claim 5,
wherein
the first application devices and/or the second application devices have distributing elements configured for distributing a sterilizing agent to mouth regions of the containers, wherein the distributing elements having a larger cross section than the mouth cross sections of the containers to be sterilized.

17. The sterilization device according to claim 5,
wherein
the first application devices and/or the second application devices are movable with respect to the containers to be sterilized in a longitudinal direction of the containers.

18. The sterilization device according to claim 5,
wherein
the first holding devices are arranged in a first position respect to a longitudinal direction of the plastic preforms and the second holding devices are arranged in a second position with respect to the longitudinal direction of the plastic preforms, and the first and second positions are different.

19. The sterilization device according to claim 6,
wherein
the first holding devices are arranged in a first position with respect to a longitudinal direction of the plastic preforms and the second holding devices are arranged in a second position with respect to the longitudinal direction of the plastic preforms, and the first and second positions are different.

* * * * *